United States Patent [19]

Sotomura et al.

[11] 4,328,218

[45] May 4, 1982

[54] **METHOD FOR THE TREATMENT OF CELLS OF *STREPTOCOCCUS PYOGENES***

[75] Inventors: Mikio Sotomura; Seiichi Iwamoto; Teruo Sawada; Shintaro Inoue, all of Osaka; Akira Suzuki, Tondabayashi; Yoshiaki Ikeda, Osaka, all of Japan

[73] Assignee: Kanebo Ltd., Tokyo, Japan

[21] Appl. No.: 211,711

[22] Filed: Dec. 1, 1980

[30] Foreign Application Priority Data

Dec. 4, 1979 [JP] Japan ................................ 54-157643

[51] Int. Cl.³ ..................... A61K 35/78; A61K 35/00; A61K 39/02
[52] U.S. Cl. .................................. 424/195; 424/123; 424/92
[58] Field of Search ................. 424/195 MS File, 92, 424/123

[56] References Cited

FOREIGN PATENT DOCUMENTS 43-6690   3/1968  Japan .
51-44617  4/1976  Japan .
55-61792  5/1980  Japan .

OTHER PUBLICATIONS

Japanese Journal of Experimental Medicine, vol. 36, pp. 161–174 (1966).

*Primary Examiner*—Donald B. Moyer
*Attorney, Agent, or Firm*—Wenderoth, Lind & Ponack

[57] ABSTRACT

A process for production of an anti-tumor agent which comprises subjecting the culture cells of the strains belonging to *Streptococcus pyogenes* in sequence to pasteurization treatment (the first step) and penicillin treatment (the second step), followed by a primary lyophilization (the third step) to obtain an intermediary preparation, and then subjecting the intermediary preparation to penicillin removal treatment (the fourth step), followed by a secondary lyophilization (the fifth step).

7 Claims, No Drawings

METHOD FOR THE TREATMENT OF CELLS OF *STREPTOCOCCUS PYOGENES*

DETAILED DESCRIPTION OF THE INVENTION

The present invention relates to a novel and excellent process for production of an anti-tumor agent comprising a cell component of *Streptococcus pyogenes* (hereinafter called *St. pyogenes* for short) having an anti-tumor activity. More particularly, it relates to a process for production of an excellent anti-tumor agent comprising a cell component of *St. pyogenes* having excellent anti-tumor activity and less side-effects and being rich in preservation stability.

In recent years, *St. pyogenes* has been cultured and anti-tumor agents prepared from its cells (hereinafter called the culture cell or live bacteria) have become to be used in actual therapy, but preparations of this sort are required to have a high anti-tumor activity and at the same time, it is required not to contain live bacteria being pathogenic bacteria.

Conventionally, various proposals have been made for the process by which to meet the said demands. The most representative is a process of holding the culture cell in aqueous solutions of salts containing penicillin at 30°–38° C., followed by lyophilizing as the penicillin is contained [Japanese Journal of Experimental Medicine, Vol. 36, p. 161–174 (1966)]. Preparations obtained by this process, however, entails such drawbacks as to have side effects from penicillin contained therein (such as shock, skin rash, pain at the time of injection and so on) and it is still hard to say that they are satisfactory in anti-tumor activity.

In this connection, preparations of this sort should preferably contain no penicillin, but nevertheless, as mentioned above, penicillin-containing preparations are still put to practical use. This is because: If penicillin is removed after the culture cell is treated with penicillin, all that is obtained is a preparation markedly lowered in anti-tumor activity [refer to Comparative Example 2 in the hereinbelow-described Table 1].

The instant inventors studied in various ways with a view to obtaining improved and excellent anti-tumor preparations, viz., preparations more improved in anti-tumor activity and freed from side effects arising from the live bacteria and penicillin or the like, in consequence of which they found a process by which to not only achieve the said object but surprisingly to be capable of obtaining excellent preparations rich in preservation stability.

The present invention will be explained in more detail as follows:

The present invention involves subjecting the culture cell to pasteurization treatment (first step) and penicillin treatment (second step), followed by a primary lyophilization (third step) to first obtain intermediary preparations and then subjecting the intermediary preparations to penicillin removing treatment (fourth step) and then a secondary lyophilization (fifth step) to obtain final preparations.

The culture cell as starting material of the present invention is obtained by culturing *St. pyogenes*. This cultivation is conducted by the known process (Japanese Patent Publication No. 43-6690) involving the using of the culture medium (such as nutrient broth) not containing fermentable carbon sources, or by the process invented by the instant inventors (Japanese Laid-Open Patent Application No. 55-61792; refer to the hereinbelow-described experimental example) which comprises positively adding fermentable carbon sources to the said culture medium and culturing *St. pyogenes* by adjusting pH of the culture medium to 5.6–7.5.

As *St. pyogenes* used in the present invention there can be used those strains belonging to known *St. pyogenes*, such as *St. pyogenes* ATCC No. 21060, *St. pyogenes* ATCC No. 21059 [for which reference should be made to the ATCC Catalogue of Strains I (1978)], *St. pyogenes* IID S-43, *St. pyogenes* IID T-3 [for which reference should be made to the JFCC Catalogue of Cultures (1979)] and so on. These strains are all publicly available.

Cells multiplied by cultivation are collected by conventional procedures, such as centrifugation and cleansed optionally in an appropriate solvent (such as water, physiological saline and so on). Using these culture cells, the first step through the five step are conducted as follows:

First, for pasteurization treatment (first step) any means will suffice as long as it is a process of substantially killing off the live bacteria without impairing the anti-tumor activity, but a process of treating the culture cell with hydrogen peroxide or monohydric alcohol is most preferred in terms of effect and readiness with which the operation is conducted.

In the case of using hydrogen peroxide, the culture cell is suspended in physiological saline, for instance, and by the addition of aqueous hydrogen peroxide in the amount of 1/20 to ⅓, preferably 1/15 to 1/5 (V/V), that of the suspension if it is based on 10% hydrogen peroxide, for instance, it is held, for instance, at −5° to 10° C., preferably 0° to 5° C., for 10 to 120 minutes, preferably for 20 to 40 minutes and after that, the cells are collected by centrifugation. Further, the concentration of hydrogen peroxide used is not limited to 10% as the above and it will do if the amount of hydrogen peroxide remains within the said range with respect to the cell suspension.

In the case of using monohydric alcohol, it is conducted by bringing the culture cell into intimate contact with the monohydric alcohol, such as by adding the monohydric alcohol to the culture cell or physiological saline suspension of the culture cell, for instance.

Available alcohols are monohydric alcohols, preferably $C_1$–$C_{12}$ aliphatic alcohols and thioalcohols. Their examples include methyl alcohol, ethyl alcohol, n-propyl alcohol, iso-propyl alcohol, n-butyl alcohol, sec-butyl alcohol, tert-butyl alcohol, n-amyl alcohol, sec-amyl alcohol, tert-amyl alcohol, iso-amyl alcohol, n-hexyl alcohol, n-octyl alcohol and benzyl alcohol, mercaptoethanol, etc., and these alcohols can be used alone or as mixtures. Of these alcohols it is ethyl alcohol that is particularly preferred.

In the case of using alcohols readily soluble in water from among said monohydric alcohols it will do to suspend the culture cell in its aqueous solution and mix together, but in the case of using alcohols sparingly soluble in water, the alcohol is added to the physiological saline suspension of the culture cell, for instance, and the two liquid layers so formed are thoroughly mixed by stirring. The amount or concentration of the alcohol used varies according to the correlations between the kind of alcohol, treating temperature and treating time, but it should preferably be used in the amount of 2 to 100 times (W/W) that of the culture cells and about 4% (W/V) or more based on the whole treating solution.

In alcohol treatment the treating temperature is set at 50° C. or less, preferably −5° to 45° C. and most preferably 0°–5° C., whereas the treating time is not specifically restricted and usually it is set at 10 to 60 minutes.

By effecting the said alcohol treatment the live bacteria could be killed off. Not only that, but it is also possible to obtain the final preparations markedly reinforced in anti-tumor activity, in particular (refer to Example 2 to Example 5 in Table 1).

The penicillin treatment (second step) of the present invention is effected by suspending the cells which have gone through pasteurization treatment (first step) in a penicillin-containing aqueous medium and holding it at 10°–50° C. for 10–60 minutes, preferably at 35°–37° C. for 20–30 minutes and then at 40°–45° C. for 20–30 minutes.

Water will suffice for the aqueous medium used in the second step, but there are cited solutions of salts, such as physiological saline or Bernheimer's Basal medium (medium comprising 675 mg of maltose, 6 ml of 20% aqueous solution of potassium dihydrogen phosphate adjusted to pH 7.0 with sodium hydroxide and 12 ml of 2% aqueous magnesium sulfate heptahydrate and 66 ml of distilled water; hereinafter called BBM for short).

As the penicillin used in the second step there are cited penicillin G, ampicillin, amoxicillin, phenethicillin, dicloxacillin, hetacillin, methicillin and salts thereof.

These penicillins are dissolved in said aqueous media and for their concentrations they are used as 5 mg (titre)/ml or more, preferably 10 mg (titre)/ml or more, and more preferably 15 to 50 mg (titre)/ml.

Further, the penicillin used in the second step does not form a cause for side effects even if used in a great deal since the penicillin is removed in the hereinbelow-described penicillin removing step (fourth step).

In the primary lyophilization (third step) of the present invention, the cell suspension (containing penicillin) obtained by way of penicillin treatment (second step) is lyophilized as such under reduced pressure generally at a temperature of 20° C. or less, preferably −10° C. or less by following conventional procedures whereby there is obtained an intermediary product.

The intermediary product so obtained contains no live bacteria and shows a considerable anti-tumor activity, but because of containing a great deal of penicillin it has side effects ascribable to the penicillin and further, it lacks in preservation stability (refer to Comparative Example 1 in Table 1).

The penicillin removal (fourth step) of the present invention is a step of removing the penicillin contained, without impairing the anti-tumor activity, from the intermediary product obtained by the primary lyophilization (third step).

It is not necessary to specifically limit the means for the removal of penicillin, unless the anti-tumor activity is impaired, but particularly preferably, it is a process of suspending the intermediary product in aqueous media (such as water, physiological saline, BBM and so on) at a temperature of 30° C. or less, preferably −5° to 5° C. whereby collecting the cells by centrifugation, and optionally by repeating this operation twice or more, cells not containing penicillin can be obtained.

If, unlike in the present invention, the culture cells are subjected in sequence to pasteurization treatment (first step) and penicillin treatment (second step) and the culture cells so treated first undergo penicillin removal and then are lyophilized, viz., the culture cells are lyophilized in the absence of penicillin, the anti-tumor activity of the preparation so obtained is markedly impaired (refer to Comparative Example 2 in Table 1).

Lastly, the secondary lyophilization (fifth step) of the present invention is conducted by suspending the cells not containing penicillin obtained by way of penicillin removal (fourth step) in an aqueous medium (such as water, physiological saline, BBM or the like), more preferably by joint use of a stabilizer and/or a vehicle, and lyophilizing the resultant suspension at the same conditions as mentioned of the primary lyophilization, for instance, by following conventional procedures as in the case of the primary lyophilization (third step) whereby the final product of the present invention is obtained.

As the stabilizer referred to here, examples include inorganic antioxidants, such as sodium thiosulfate, sodium pyrosulfite, sodium hydrogensulfite and so on, inert proteins, such as gelatin, albumin and so on, amino acids, such as methionine, arginine, cystine and so on, polysaccharides, such as dextran, dextran sulfate, starch and so on, and further, sodium hydrogencarbonate and so forth, and they can be used alone or in combination of several members.

As the vehicle disaccharides, those such as maltose and lactose, are representative, but it will not be limited to these ones.

The final preparation of the present invention is good in anti-tumor activity, markedly improved in the respect of side effects because of not containing the live bacteria and penicillin and does not go lower in anti-tumor activity even if preserved for a long term.

The characteristic feature of the present invention, as mentioned above, consists in obtaining improved and excellent anti-tumor preparations by subjecting the culture cells in sequence to pasteurization treatment (first step), penicillin treatment (second step), primary lyophilization (third step), penicillin removal (fourth step) and secondary lyophilization (fifth step).

Contrary to the present invention, products obtained by omitting the penicillin removal (fourth step) as in Comparative Example 1 entail side effects of penicillin. Not only that, but they lack in preservation stability. Further, preparations obtained by lyophilizing in the absence of penicillin as in Comparative Example 2 are inferior in both aspects of anti-tumor activity and preservating stability.

The preparations of the present invention can be used in the actual therapy by following the same procedures as with the conventionally known preparations. For instance, the preparation of the present invention is suspended in physiological saline or aqueous glucose solution and it can be administered by hypodermic, intramuscular or intravenous injection in the amount of 0.02 to 1.0 mg as the cell component for successive days or 2 to 3 times a week.

The present invention will be explained by referring to Examples and Comparative Examples as follows:

Further, the culture cells and their suspensions, starting materials used in the respective experiments, were prepared as per Experimental Example to follow.

Acute toxicity ($LD_{50}$) and anti-tumor activity (in vitro and in vivo) of each of preparations indicated in Table 1 were measured in the following manner.

EXPERIMENTAL EXAMPLE

Example of preparation of the culture cell as starting material of the present invention will be shown as follows: 150 ml of a culture solution of *Streptococcus pyogenes* ATCC 21060 cultured in advance by the use of nutrient broth (Kyokuto Seiyaku) was inoculated into a culture medium (pH 7.2 to 7.4) obtained by dissolving 60 g of soy polypeptone broth [Phytone ® (BBL)] in 2,000 ml of distilled water and steam sterilizing at 121° C. for 20 minutes.

Then an aqueous glucose solution was mixed in such a manner for the glucose concentration to reach 0.4% (W/W) based on the whole culture solution and the cells were cultured at 37° C. for 20 hours by adjusting pH to 6.5 with 5 N NaOH solution. The culture solution was cooled with ice and then the cells were collected by cold centrifugation. The cells so obtained were suspended in 80 ml of physiological saline. 80 ml of the suspension obtained in such a manner contained 1400 to 1600 mg, 1500 mg on the average (average cell concentration 18.75 mg/ml), of cells.

Acute toxicity ($LD_{50}$)

A group of 5 mice 4 weeks old (ddy strain female) were tested.

The respective samples (preparations) were placed in physiological saline to prepare cell suspensions in the respective concentrations. The cell suspensions in the respective concentrations were intravenously injected into the tails of the mice in the amount of 0.01 ml per gram of the weight of the mouse and $LD_{50}$ was calculated by following the Weil procedure on the basis of results of observations made for 7 days.

In vitro anti-tumor activity

Yoshida sarcoma cells were intraperitoneally transferred into rats and 5 days later their ascites were taken and centrifuged at about 120 G for 7 minutes to collect Yoshida sacroma cells. This one was suspended in a 20% horse serum-added Eagle MEM culture medium in such a manner for the cell concentration to reach $5 \times 10^4$ cells/ml whereby there was prepared a cell solution to test.

Sample was diluted with physiological saline to prepare sample solutions in various concentrations. 0.1 ml of each sample solution and 0.9 ml of said cell solution to test were placed in test tubes, tightly stoppered and cultured at 37° C. for 48 hours to count numbers of live cells with respect to each sample solution in the respective concentrations.

As control, on the other hand, 0.1 ml of physiological saline alone was added to 0.9 ml of the cell solution to test and it was likewise cultured to count numbers of its live cells.

In the next place, cell multiplication inhibition percentages (%) of each sample solution was determined by the following equation.

$$\text{Cell multiplication inhibition percentage (\%) of each sample solution} = \left(1 - \frac{\text{Numbers of live cells of each sample solution}}{\text{Numbers of live cells of control test}}\right) \times 100$$

By plotting the concentrations of sample solutions on the semilogarithmic graph paper as abscissa (logarithmic scale) and cell multiplication inhibition percentages of each sample solution as ordinate, a concentration ($IC_{50}$, mg/ml) indicating 50% cell multiplication inhibition was determined and set as in vitro antitumor activity of the sample concerned.

Further, the measurement of in vitro anti-tumor activity was made not only of the preparation immediately after its preparation but also of the preparation preserved at 60° C. for 6 months in a condition where it is kept in a closely stoppered vial.

In vivo anti-tumor activity $1 \times 10^6$ of Ehrlich ascites carcinoma cells per mouse were transferred into a group of 10 mice (ddy strain female, about 5 weeks old) and they were intraperitoneally inoculated with 0.2 ml of physiological saline suspension of the sample (prepared in such a manner as to reach 1 mg/ml in the dry cell concentration) for 5 successive days to investigate numbers of mice surviving after 30 days.

Further, as control, 0.2 ml of physiological saline alone was inoculated intraperitoneally for 5 successive days and on that occasion, numbers of mice surviving after 30 days were zero (0).

EXAMPLE 1

(1) The first step (pasteurization treatment with hydrogen peroxide)

By the addition of 8 ml of 10% aqueous hydrogen peroxide 80 ml of culture cell susension cultured and prepared according to said Experimental Example was held at 0° C. for 30 minutes and then centrifuged to collect cells. The cells were twice cleansed with 240 ml of cold physiological saline.

Then, the cells were suspended in about 250 ml of cold BBM and so adjusted as to reach 10 in the absorbance at 660 nm (cell concentration 6 mg/ml).

(2) The second step (penicillin treatment with penicillin G)

200 ml of the BBM suspension (containing about 1200 mg of cells) obtained in the first step was taken and by the addition of 200 ml of aqueous penicillin G potassium salt solution [containing 54,000 units of penicillin G potassium salt per ml (about 34 mg (titre)/ml)] it was held at 37° C. for 20 minutes and then at 45° C. for 30 minutes whereby there was obtained 400 ml of penicillin treated suspension (of which the 200 ml was used in the third step of the instant experiment and of which the 100 ml was used in Comparative Example 2).

(3) The third step (primary lyophilization)

20 ml each of 200 ml of the penicillin treated suspension (containing about 600 mg of cells) obtained in the second step were poured respectively into 10 vials (with an inner capacity of 100 ml), prelyophilized at −30° C. for 4 hours (under normal pressure) and then depressurized (about 0.05 mmHg) at such temperature conditions as not to exceed 20° C. for 4 hours whereby there were obtained intermediary preparations. (Of these intermediary preparations 5 vials of them were used in the fourth step of the instant experiment and the remaining 5 vials were used in Comparative Example 1.)

(4) The fourth step (penicillin removal)

40 ml each of cold physiological saline were poured respectively into 5 vials of each intermediary preparation obtained in the third step and thoroughly mixed to collect cells (about 300 mg) by centrifugation. The cells were put together, suspended in 200 ml of cold physiological saline and then centrifuged whereby there were obtained cells not containing the penicillin G potassium salt.

(5) The fifth step (secondary lyophilization)

240 mg of the cells not containing penicillin obtained in the fourth step was suspended in about 80 ml of a mixed solution of 2.5% aqueous maltose solution and 3% aqueous sodium thiosulfate solution [4:1 (V/V)] and so adjusted the cell concentration as to reach 3 mg per ml.

Then, 1 ml each of the resultant suspension (containing 3 mg of cells) were poured respectively into vials (with an inner capacity of 15 ml) and lyophilized at the same conditions as used in the said primary lyophilization (third step) to obtain the final preparations of the present invention.

The final preparation (containing 3 mg of cells in one vial) obtained in Example 1, as Table 1 indicates, is low in toxicity, good in anti-tumor activity and rich in preservation stability.

EXAMPLE 2-EXAMPLE 5

The following are experiments in which pasteurization treatment was conducted by using ethyl alcohol (Example 2), iso-propyl alcohol (Example 3), tert.-butyl alcohol (Example 4) and benzyl alcohol (Example 5) instead of hydrogen peroxide of Example 1.

(1) The first step (pasteurization treatment with monohydric alcohol)

In the respective Examples, 20 ml of culture cell suspension (containing about 375 mg of cells) cultured and prepared according to the said Experimental Example was taken and centrifuged to collect cells. The cells so collected were used as starting material.

In the case of readily soluble in water ethyl alcohol, isopropyl alcohol and tert.-butyl alcohol, the said cells were suspended in 20 ml of each 80% aqueous solution of the respective alcohols and held at 0°–5° C. for 30 minutes.

In the case, on the other hand, of sparingly soluble in water benzyl alcohol, 10 ml of benzyl alcohol and 10 ml of water were poured on the said cells and two liquid layers so formed were held at 0°–5° C. for 30 minutes by thoroughly stirring by means of magnetic stirrer.

Then, in the respective Examples, the alcohol treated solution was centrifuged to collect cells. The cells were twice cleansed with 60 ml of cold physiological saline and suspended in about 50 ml of cold BBM and so adjusted as to reach 10 in the absorbance at 660 nm (cell concentration 6 mg/ml).

(2) The second step (penicillin treatment), third step (primary lyophilization), fourth step (penicillin removal) and fifth step (secondary lyophilization)

Using 50 ml of BBM suspension (containing about 300 mg of cells) obtained in the first step in each of the Examples, the second step through the fifth step were conducted in sequence in quite the same manner as in Example 1. In this way, there were obtained the respective final products of Examples 2-5.

The final products (containing 3 mg of cells in one vial) so obtained, as Table 1 indicates, are each low in toxicity, very good in anti-tumor activity, in particular, and rich in preservation stability.

EXAMPLE 6

Penicillin treatment with conducted with ampicillin instead of penicillin G of Example 1.

(1) The first step (pasteurization treatment with hydrogen peroxide)

Using 20 ml of culture cell suspension (containing about 375 mg of cells) cultured and prepared according to the said Experimental Example, treatment was effected with hydrogen peroxide in quite the same manner as in Example 1 to obtain BBM suspension.

(2) Second step (penicillin treatment with ampicillin)

50 ml of aqueous solution of ampicillin (aminobenzyl penicillin sodium salt) [containing 60 mg (titre) of ampicillin per ml] was added to 50 ml of the BBM suspension (containing about 375 mg of cells) obtained in the first step and the mixture was held at 37° C. for 30 minutes and then at 45° C. for 30 minutes to obtain 100 ml of penicillin treated suspension.

(3) The third step (primary lyophilization), fourth step (penicillin removal) and fifth step (secondary lyophilization)

Using the penicillin treated suspension (containing about 300 mg of cells) obtained in the second step, the third step through the fifth step were conducted in quite the same manner as in Example 1 to obtain the final product.

This final product (containing 3 mg of cells in one vial), as Table 1 indicates, is low in toxicity and excellent in anti-tumor activity as well as in preservation stability.

COMPARATIVE EXAMPLE 1

The following is the formulation of a preparation in the case of omitting the penicillin removal (fourth step).

Five (5) vials of the intermediate preparation (containing about 300 mg of cells and a great deal of penicillin G) obtained in the third step (primary lyophilization) of Example 1 were suspended as such, without effecting the penicillin removal, in about 100 ml of a mixed solution of 2.5% aqueous maltose solution and 3% aqueous sodium thiosulfate solution [4:1 (V/V)] in like manner as in the case of the fifth step of Example 1 and so adjusted as to reach 3 mg/ml in the cell content and the suspension so obtained was lyophilized at the same conditions.

The preparation (containing 3 mg of cells in one vial) obtained in this Comparative Example 1, as Table 1 indicates, shows toxicity based on penicillin and is inferior in preservation stability.

COMPARTIVE EXAMPLE 2

Comparative Example 2 correspond to experiment in which the penicillin removal is effected prior to the third step (primary lyophilization) of Example 1, and it was conducted as follows:

Of 400 ml of the penicillin treated suspension obtained in the second step (penicillin treatment with penicillin G) of Example 1 the 100 ml (containing about 300 ml of cells) was taken and centrifuged to collect cells. The cells were twice cleansed with 200 ml of cold physiological saline to obtain cells not containing penicillin G.

Then, the cells so obtained (about 240 mg) were suspended in 80 ml of cold BBM and the resultant suspension was lyophilized at the same conditions as in the case of the third step (primary lyophilization) of Example 1. Further, the product was suspended in 80 ml of a mixed solution of 2.5% aqueous maltose solution and 3% aqueous sodium thiosulfate solution [4:1 (V/V)] in like manner as in the case of the fifth step (secondary lyophilization) of Example 1 and likewise lyophilized.

The preparation (containing 3 mg of cells in one vial) obtained in this Comparative Example 2, as Table 1 indicates, is markedly low in anti-tumor activity.

TABLE 1

| Preparations | Penicillin content (penicillin unit/vial) | $LD_{50}$ (mg/kg) | Anti-tumor activity immediately after preparation | | Anti-tumor activity after preservation at 60° C. for 6 months |
|---|---|---|---|---|---|
| | | | in vivo* | in vitro ($IC_{50}$) | in vitro ($IC_{50}$) |
| Example 1 | 0 | >50 | 10/10 | 0.0112 | 0.018 |
| Example 2 | 0 | >50 | 10/10 | 0.003 | 0.004 |
| Example 3 | 0 | >50 | 10/10 | 0.004 | 0.006 |
| Example 4 | 0 | >50 | 10/10 | 0.003 | 0.004 |
| Example 5 | 0 | >50 | 10/10 | 0.002 | 0.003 |
| Example 6 | 0 | >50 | 10/10 | 0.018 | 0.023 |
| Comparative Example 1 | 27,000 | 15 | 10/10 | 0.015 | >0.3 |
| Comparative Example 2 | 0 | >50 | 2/10 | >0.3 | >0.3 |

*Number of mice survived/number of test mice

NOTE:

(1) Example 1. Pasteurization treatment with hydrogen peroxide (first step), penicillin treatment with penicillin G potassium salt (second step), primary lyophilization (third step), penicillin G removal (fourth step) and secondary lyophilization (fifth step) were conducted in sequence.

(2) Example 2 through Example 5. Experiments were conducted in quite the same manner as in Example 1 except that ethyl alcohol (Example 2), isopropyl alcohol (Example 3), tert.-butyl alcohol (Example 4) and benzyl alcohol (Example 5) were substituted for hydrogen peroxide in the pasteurization treatment (first step).

(3) Example 6. Experiment was conducted in quite the same manner as in Example 1 except that ampicillin was substituted for penicillin G potassium salt in the penicillin treatment (second step).

(4) Comparative Example 1. Experiment was conducted in quite the same manner as in Example 1 except that the penicillin removal (fourth step) was omitted.

(5) Comparative Example 2. Penicillin removal was effected immediately after the penicillin treatment (second step) and then the primary lyophilization and secondary lyophilization were conducted.

What we claim are:

1. A method for treating cells of *Streptococcus pyogenes* having an anti-tumor activity which comprises
   (1) treating the cells with hydrogen peroxide at a temperature in the range of −5° C. to 10° C. or with a monohydric alcohol having carbon numbers of 1–12 at a temperature in the range of −5° C. to 45° C. to pasteurize the cells,
   (2) suspending the pasteurized cells in a penicillin-containing aqueous medium at a temperature of 10° C. to 50° C.,
   (3) lyophilizing the cells,
   (4) washing the lyophilized cells with an aqueous medium at a temperture of not more than 30° C. to remove the penicillin from the cells, and
   (5) lyophilizing the thus obtained cells.

2. A method according to claim 1 in which at least one strain selected from the group consisting of *St. pyogenes* ATCC No. 21060, *St. pyogenes* ATCC No. 21059, *St. pyogenes* IID S-43 and *St. pyogenes* IID T-3 is used as the *Streptococcus pyogenes* strain.

3. A method according to claim 1 in which the cells are treated with ethanol to pasteurize the cells.

4. A method according to claim 1 in which the pasteurized cells are suspended in a penicillin-containing physiological saline or Bernheimer's Basal medium.

5. A method according to claim 1 in which the concentration of penicillin in the penicillin-containing aqueous medium is set at 5 to 50 mg (titre)/ml.

6. A method according to claim 1 in which washing the lyophilized cells with an aqueous medium to remove the penicillin is conducted by suspending said cells in water, physiological saline or Bernheimer's Basal medium.

7. A method according to claim 1 in which the lyophilization of step (5) of claim 1 is conducted after addition of at least one of a stabilizer and a disaccharide to the cells, said stabilizer being selected from the group consisting of inorganic antioxidants, inert proteins, amino acids, polysaccharides and sodium hydrogencarbonate.

* * * * *